United States Patent
Aoki et al.

(10) Patent No.: US 8,834,233 B2
(45) Date of Patent: Sep. 16, 2014

(54) METHOD OF MANUFACTURING IMPLANT AND METHOD OF MANUFACTURING ARTIFICIAL DENTAL ROOT

(75) Inventors: Hideki Aoki, Tokyo (JP); Masashi Toyama, Aichi (JP); Hiroto Fujimaki, Tokyo (JP); Yuki Hashimoto, Tokyo (JP)

(73) Assignee: Yamahachi Dental Mfg., Co., Aichi (JP)

( * ) Notice: Subject to any disclaimer, the term of this patent is extended or adjusted under 35 U.S.C. 154(b) by 337 days.

(21) Appl. No.: 12/441,219

(22) PCT Filed: Dec. 9, 2008

(86) PCT No.: PCT/JP2008/003664
§ 371 (c)(1),
(2), (4) Date: Jun. 7, 2010

(87) PCT Pub. No.: WO2009/075095
PCT Pub. Date: Jun. 18, 2009

(65) Prior Publication Data
US 2010/0243429 A1 Sep. 30, 2010

(30) Foreign Application Priority Data
Dec. 11, 2007 (JP) .................................. 2007-319222

(51) Int. Cl.
B24C 1/06 (2006.01)
A61C 8/00 (2006.01)
A61F 2/28 (2006.01)
B24C 11/00 (2006.01)
A61C 13/00 (2006.01)
A61F 2/30 (2006.01)

(52) U.S. Cl.
CPC ............... *B24C 1/06* (2013.01); *A61F 2/30771* (2013.01); *B24C 11/00* (2013.01); *A61F 2/3094* (2013.01); *A61C 13/0007* (2013.01); *A61F 2002/30906* (2013.01); *A61C 8/00* (2013.01); *A61C 2008/0046* (2013.01)
USPC .......................................... 451/39; 433/201.1

(58) Field of Classification Search
USPC .................. 623/16.11, 23.57; 451/39; 433/88, 433/201.1
IPC ................... A61C 8/00; A61F 2/28; B24C 1/06
See application file for complete search history.

(56) References Cited

U.S. PATENT DOCUMENTS

| | | | | |
|---|---|---|---|---|
| 4,149,893 A * | 4/1979 | Aoki et al. | | 106/35 |
| 4,222,128 A * | 9/1980 | Tomonaga et al. | | 623/23.51 |
| 4,451,235 A * | 5/1984 | Okuda et al. | | 433/201.1 |
| 4,708,652 A * | 11/1987 | Fujiu et al. | | 433/201.1 |
| 5,441,536 A * | 8/1995 | Aoki et al. | | 427/2.27 |
| 5,833,959 A * | 11/1998 | Atsumi et al. | | 424/57 |
| 5,934,287 A * | 8/1999 | Hayashi et al. | | 128/898 |
| 6,129,928 A * | 10/2000 | Sarangapani et al. | | 424/423 |
| 6,143,948 A * | 11/2000 | Leitao et al. | | 424/422 |
| 6,302,913 B1 * | 10/2001 | Ripamonti et al. | | 623/16.11 |
| 6,485,304 B2 * | 11/2002 | Beerstecher et al. | | 433/88 |
| 6,720,023 B1 * | 4/2004 | Kim et al. | | 427/2.27 |
| 6,969,501 B2 * | 11/2005 | Sapieszko et al. | | 423/305 |
| 7,048,792 B2 * | 5/2006 | Axen et al. | | 106/692 |
| 7,749,429 B2 * | 7/2010 | Furuzono et al. | | 419/23 |
| 8,119,183 B2 * | 2/2012 | O'Donoghue et al. | | 427/2.1 |
| 2001/0053406 A1 * | 12/2001 | Layrolle et al. | | 427/2.27 |
| 2002/0128723 A1 * | 9/2002 | Hayashi et al. | | 623/23.56 |
| 2003/0215484 A1 * | 11/2003 | Axen et al. | | 424/423 |
| 2004/0146752 A1 * | 7/2004 | Axen et al. | | 428/702 |
| 2004/0153165 A1 * | 8/2004 | Li et al. | | 623/23.57 |
| 2004/0158330 A1 * | 8/2004 | Muller et al. | | 623/23.57 |
| 2005/0000819 A1 * | 1/2005 | LeGeros et al. | | 205/104 |
| 2006/0062925 A1 * | 3/2006 | Rohanizadeh et al. | | 427/430.1 |
| 2006/0286509 A1 * | 12/2006 | Bassett et al. | | 433/173 |
| 2007/0037122 A1 * | 2/2007 | Bassett et al. | | 433/173 |
| 2007/0111164 A1 * | 5/2007 | Saade et al. | | 433/174 |
| 2008/0274671 A1 * | 11/2008 | O'Donoghue et al. | | 451/39 |
| 2008/0306554 A1 * | 12/2008 | McKinley | | 606/301 |
| 2009/0010990 A1 * | 1/2009 | Little et al. | | 424/423 |
| 2009/0035722 A1 * | 2/2009 | Balasundaram et al. | | 433/201.1 |
| 2009/0110748 A1 * | 4/2009 | Okada | | 424/602 |
| 2009/0220914 A1 * | 9/2009 | Gershenzon | | 433/174 |
| 2009/0281289 A1 * | 11/2009 | Rheinnecker et al. | | 530/427 |
| 2010/0010632 A1 * | 1/2010 | Bourges et al. | | 623/16.11 |
| 2010/0070046 A1 * | 3/2010 | Steinberg | | 623/22.25 |
| 2010/0098632 A1 * | 4/2010 | Russell et al. | | 424/1.77 |
| 2010/0185297 A1 * | 7/2010 | Steinberg | | 623/22.21 |
| 2010/0211158 A1 * | 8/2010 | Haverty et al. | | 623/1.15 |
| 2010/0243429 A1 * | 9/2010 | Aoki et al. | | 204/192.15 |
| 2011/0059149 A1 * | 3/2011 | Little et al. | | 424/423 |
| 2013/0078476 A1 * | 3/2013 | Riman et al. | | 428/469 |

FOREIGN PATENT DOCUMENTS

| JP | 3076637 B2 | 8/2000 |
|---|---|---|
| JP | H0557011 A * | 8/2000 |
| JP | 2003342113 A * | 12/2003 |

OTHER PUBLICATIONS

Machine translation of JPH0557011A.*
Machine translation of JP 2003342113 A.*
Espacenet English Abstract for JP3076637, published Aug. 14, 2000 (2 pages).

* cited by examiner

*Primary Examiner* — Lee D Wilson
*Assistant Examiner* — Marc Carlson
(74) *Attorney, Agent, or Firm* — Osha Liang LLP

(57) ABSTRACT

A method for producing an implant whose surface is roughened by the sandblast method using shot material containing fluoroapatite. Fluoroapatite, compared to hydroxyapatite, has poor biocompatibility, but is superior in hardness. It also has a property of being dissolved in acid. As a result, by the sandblast method using shot material containing fluoroapatite, the surface roughening is performed quite effectively, and shot materials remained on the surface can easily be removed by acid.

11 Claims, No Drawings

METHOD OF MANUFACTURING IMPLANT AND METHOD OF MANUFACTURING ARTIFICIAL DENTAL ROOT

BACKGROUND OF THE INVENTION

1. Field of the Invention

The present invention relates to a method for producing implants and artificial dental roots. In particular, for example, the present invention relates to a method for producing an artificial dental root wherein the surface of an artificial dental root is roughened by the sand blast method using shot material containing fluoroapatite, and removing the shot material by dissolving it.

2. Description of the Related Art

Japanese Patent Application Laid-Open publication No. 10-99438 discloses a method for producing a dental implant in which the sand blast method is used for surface treatment of the dental implant. In the method disclosed in this bulletin, hydroxyapatite is used as shot material (blast grain). And, in this bulletin, hydroxyapatite is intentionally embedded in the surface of a dental implant, and is used as bone forming promoter after the dental implant is planted in a jaw bone (see the abstract, etc.).

Hydroxyapatite is a little decomposed at high temperature equal to or more than 1000° C. Hence it is difficult to produce a sophisticated sintered body from hydroxyapatite. In addition, since hydroxyapatite dose not have enough hardness compared to fluoroapatite, it is difficult to perform a desired surface roughening on the surface of the implant appropriately. On the other hand, shot material which is used in the conventional sand blast method is so hard that it scratches the surface of an implant leaving deep scars or cracks, thereby shortening the implant's durability. Also, since the conventional shot material has poor biocompatibility and is not suitable for bone regeneration, the shot material had to be removed from an implant after the sand blast method is performed to roughen the surface thereof. However, there was a problem that shot material could not be completely removed physically and chemically.

The object of the present invention is to provide a method for producing implants which have preferred roughened surfaces, and from which shot material is removed appropriately.

The object of the present invention is to provide implants whereon homogeneous and highly refined hydroxyapatite coating is firmly combined.

SUMMARY OF THE INVENTION

The present invention basically relates to a method for producing an implant wherein the surface thereof is roughened by the sand blast method using shot material containing fluoroapatite. Although fluoroapatite has a little poor biocompatibility when compared with hydroxyapatite, it has a sophisticated crystal structure which makes implants made from fluoroapatite difficult to be decomposed at high temperatures. Thus the sophisticated sintered body of fluoroapatite produced at high sintering temperature is harder than that of hydroxyapatite, and also it has moderate hardness which is tender when compared with conventional shot material such as alumina. On the other hand, it has a property to be dissolved in acid easily. As a result, by performing surface roughening by the sand blast method using shot material containing fluoroapatite, an implant having quite preferred roughened surface can be obtained, and remaining shot materials can easily be removed by acid.

The first aspect of the present invention relates to a method for producing an implant comprising a step of roughening the surface of an implant by the sand blast method, wherein the step of roughening the surface of an implant includes a step of colliding shot material with the surface of the implant, the shot material comprising fluoroapatite.

A preferred embodiment of the first aspect of the present invention relates to the above described method for producing an implant, wherein the step of roughening the surface of an implant is a step to roughen the surface thereof so that the arithmetic mean deviation of the profile Ra, arithmetic average of absolute values, of the surface thereof becomes in the range from 0.3 μm to 3 μm.

Since fluoroapatite is used as shot material, the surface of the implant can easily be roughened so that the range of the arithmetic mean deviation of the profile (Ra) of the surface thereof becomes in the range from 0.3 μm to 3 μm. In this way, by sputter coating in particular, highly refined hydroxyapatite thin film which has excellent adhesiveness to base materials such as metals can be homogeneously formed.

A preferred embodiment of the first aspect of the present invention relates to one of the above described methods for producing an implant, wherein the shot material comprising fluoroapatite is screened with a screen having mesh openings from 12 to 100 mesh.

By using the above described shot material, as demonstrated in examples described below, an implant having a preferred surface roughness can be produced.

A preferred embodiment of the first aspect of the present invention relates to one of the above described methods for producing an implant, wherein the implant is an artificial dental root. A preferred embodiment of the first aspect of the present invention relates to one of the above described methods for producing an implant, wherein the implant is an artificial dental root, and wherein the step of roughening the surface of an implant is a step to roughen the surface of the root part of the artificial dental root so that the arithmetic mean deviation of the profile (Ra) of the surface thereof becomes in the range from 0.3 μm to 3 μm.

As demonstrated in examples described below, the method for producing an implant of the present invention can effectively be used for a method for producing an artificial dental root, wherein the surface of the root part thereof is roughened and then coated with a preferred hydroxyapatite coating.

A preferred embodiment of the first aspect of the present invention relates to one of the above described methods for producing an implant, further comprising a step of removing shot material, performed after the step of roughening the surface of an implant, by putting acid on the implant, the shot material being collided with the surface of the implant and attached thereto.

By the sand blast method, shot materials are cut into the surface of an implant. In the present invention, however, since fluoroapatite is used as shot material, it can be easily removed from the surface of an implant by dissolving with acid.

A preferred embodiment of the first aspect of the present invention relates to one of the above described methods for producing an implant, wherein the acid is hydrochloric acid aqueous solution of concentration ranging from 1 N to 6 N, or nitric acid aqueous solution of concentration ranging from 1 N to 6 N, and wherein the step of removing shot material comprises a step of soaking the implant into the hydrochloric acid aqueous solution or the nitric acid aqueous solution for from 1 minute to 10 minutes.

In the present invention, shot material containing fluoroapatite is used. Thus fluoroapatite can easily be removed from the surface of an implant by effectively dissolving it.

A preferred embodiment of the first aspect of the present invention relates to one of the above described methods for producing an implant, wherein a coating step of sputter coating calcium phosphate based material film on the implant after the step of removing shot material, and a hydrothermal treatment step using alkali aqueous solution, performed after the coating step.

Since the surface of the implant is roughened as explained above, it can be effectively coated with a hydroxyapatite (calcium phosphate based material) coating (film) by sputtering techniques. Furthermore, in this coating process, hydroxyapatite and the like is strongly combined with base material and homogeneously coated on the surface, so the hydroxyapatite coating is not removed, thereby being able to obtain a preferred implant.

A preferred embodiment of the first aspect of the present invention relates to one of the above described methods for producing an implant, wherein the pH range of the alkali aqueous solution is from pH 9 to pH 11. In particular, the preferred embodiment of the first aspect of the present invention relates to one of the above described methods for producing an implant, wherein the pH range of the alkali aqueous solution is from pH 9 to pH 11, and wherein in the hydrothermal treatment step, the implant is soaked in the alkali aqueous solution in the temperature range from 100° C. to 150° C. for from 3 hours to 24 hours.

As demonstrated in the example, a quite preferred implant can be obtained by performing the above described hydrothermal treatment. Impurities are generated by sputtering. By performing the above described hydrothermal treatment, the impurities can be removed. Also, hydroxyapatite coating which is formed by sputtering can be crystallized, thereby obtaining a preferred implant. Namely, by performing the above described hydrothermal treatment, an implant having homogeneous and highly refined hydroxyapatite coating strongly combined thereto can be obtained.

The second aspect of the present invention relates to a method for producing an artificial dental root comprising: a step of roughening the surface of an artificial dental root by sand blast, wherein the step of roughening the surface of an artificial dental root includes a step of colliding shot material with the surface of the artificial dental root, the shot material comprising fluoroapatite, wherein the surface of the root part of the artificial dental root is roughened so that the arithmetic mean deviation of the profile (Ra) of the surface thereof becomes in the range from 0.3 μm to 3 μm, and wherein the shot material comprising fluoroapatite is screened with a screen having mesh openings from 12 to 100 mesh, a step of removing shot material, performed after the step of roughening the surface of the artificial dental root, by putting acid on the artificial dental root, the shot material being collided with the surface of the artificial dental root and attached thereto, wherein the acid is hydrochloric acid aqueous solution of concentration ranging from 1 N to 6 N, sulfuric acid aqueous solution, nitric acid aqueous solution, or these compound acid aqueous solution of concentration ranging from 1 N to 6 N, and wherein the step of removing shot material comprises a step of soaking the artificial dental root into the hydrochloric acid aqueous solution or the nitric acid aqueous solution for from 1 minute to 10 minutes, a coating step for sputter coating hydroxyapatite film on the artificial dental root after the step of removing shot material, and a hydrothermal treatment step performed with alkali aqueous solution, performed after the coating step, wherein the pH range of the alkali aqueous solution is from pH 9 to pH 11, and wherein the artificial dental root is soaked in the alkali aqueous solution in the temperature range from 100° C. to 150° C. for from 3 hours to 24 hours.

The present invention can provide a method for producing an implant having a preferred roughened surface, from which shot material is removed properly.

The present invention can provide an implant having homogeneous and highly refined hydroxyapatite coating strongly combined thereto can be obtained.

DESCRIPTION OF THE PREFERRED EMBODIMENTS

Hereinafter, embodiments of the present invention are explained. The first aspect of the present invention relates to a method for producing an implant comprising a step of roughening the surface of an implant by the sand blast method, wherein the step of roughening the surface of an implant includes a step of colliding shot material with the surface of the implant, the shot material comprising fluoroapatite.

In the present specification, "fluoroapatite" is identical to a material called "fluorine apatite", wherein fluorine atom is replaced with a hydroxyl group in apatite. Although fluoroapatite has poor biocompatibility when compared with hydroxyapatite, it is excellent in hardness. On the other hand, it has a property to be dissolved in acid easily. As a result, by performing surface roughening of an implant by the sand blast method using shot material containing fluoroapatite, an implant having quite preferred roughened surface can be obtained, and remaining shot materials can easily be removed therefrom by acid. "Sand blast method" is a method for roughening a portion where surface roughening is to be performed by colliding hard particles with the portion.

The shot material used in a step of roughening the surface is preferred to be composed mostly of fluoroapatite, and may be composed exclusively of fluoroapatite. Hydroxyapatite is an example of shot material other than fluoroapatite. Fluoroapatite, in particular, is fluoroapatite ceramics which is sintered at the temperature range from $9 \times 10^{2}$° C. to $1.5 \times 10^{3}$° C.

The shot material is preferred to be screened with a screen having mesh openings from 12 mesh (opening 1.4 mm) to 100 mesh (opening 150 μm). As demonstrated in the examples, an implant having preferred roughened surface can be produced by using the above shot material. The shot material may be screened with a screen having mesh openings from 30 mesh to 60 mesh. Note that "mesh" is a unit of a sieve, which indicates the number of apertures per one inch in length. For example, a sieve with 14 mesh means a mesh having 14 apertures per one inch in length.

The step of roughening the surface is preferred to be performed so that the rage of the arithmetic mean deviation of the profile (Ra) of the surface thereof becomes in the range from 0.3 μm to 3 μm. The range may also be from 0.5 μm to 2 μm. An implant having the above described roughened surface can be produced from the above shot material by the sand blast method with gas charge being injected at the range from 0.2 to 2 atmospheric pressure.

Namely, in the present invention, since fluoroapatite is used as shot material, the surface of an implant can be roughened so that the rage of the arithmetic mean deviation of the profile (Ra) of the surface thereof becomes from 0.3 μm to 3 μm. In this way, by sputter coating in particular, highly refined hydroxyapatite thin film which has excellent adhesiveness to base materials such as metals can be homogeneously formed. Note that the explanation of the arithmetic mean deviation of the profile (Ra) is described in JISB0601 (1994), etc.

The examples of implants of the present specification are an artificial bone such as an artificial joint, and an artificial dental root. In particular, a preferred implant of the present invention is an artificial dental root. Also, in the present invention, it is preferred that a part or the entire surface of a root part be roughened. As demonstrated in examples described below, the method for producing an implant of the present invention can effectively be used for a method for producing an artificial dental root, wherein the surface of the root part thereof is roughened and then coated with a preferred hydroxyapatite coating.

The comparison between the present invention using shot material containing fluoroapatite and the prior art is shown in the table 1 below.

TABLE 1

|  | hydroxyapatite | conventional shot material | shot material of the present invention |
|---|---|---|---|
| hardness | X | ⊚ | ○ |
| acid solubility | ⊚ | X | ⊚ |
| Ra control | X | ○ | ⊚ |
| biocompatibility | ⊚ | X | ○ |

It can clearly be seen from the table 1 that the shot material of the present invention is superior in surface roughening compared to the conventional shot material.

A preferred embodiment of the first aspect of the present invention relates to one of the above described methods for producing an implant, further comprising a step of removing shot material, performed after the step of roughening the surface of an implant, by putting acid on the implant, the shot material being collided with the surface of the implant and attached thereto.

By the sand blast method, shot materials are cut into the surface of an implant. In the present invention, however, since fluoroapatite is used as shot material, it can be easily removed from the surface of an implant by dissolving fluoroapatite with acid.

The examples of acid used in the step of removing shot material include a 1 to 6 N hydrochloric acid aqueous solution and a 1 to 6 N nitric acid aqueous solution. The acid may be 1 N to 3 N, and also may be 1 N to 2 N. The step of removing shot material includes, for example, a step of soaking the implant in the hydrochloric acid aqueous solution or the nitric acid aqueous solution for from 1 minute to 10 minutes. In the present invention, since fluoroapatite is used as shot material, it can easily be removed from an implant by effectively dissolving fluoroapatite.

A preferred embodiment of the first aspect of the present invention relates to one of the above described methods for producing an implant, further comprising a coating step of sputter coating calcium phosphate based material film on the implant after the step of removing shot material, and a hydrothermal treatment step using alkali aqueous solution, performed after the coating step. An example of a calcium phosphate based material coating is a hydroxyapatite coating. In the step of sputter coating, for example, a method disclosed in Japanese Unexpected Patent Application Publication No. 2005-76113 is used. The specific steps of the method are as follows. A target of calcium phosphate material is placed at a target support member. A certain level of vacuum in a vacuum chamber is achieved by exhausting air in the vacuum chamber from a gas exhausting member such as a vacuum pump. Argon gas, for example, is injected into the vacuum chamber from a gas injection member, and argon ions are collided with the target. Then atoms or molecules comprising the target evaporate with high energy, colliding with an implant. As a result, a thin layer of homogeneous thickness containing target molecules is formed on the implant. This thin layer, which is obtained by sputtering, firmly combined with the implant. The target is material which evaporates by sputtering and deposited on the implant. The examples of suitable target material include hydroxyapatite or α-TCP which is a precursor of hydroxyapatite (tricalcium phosphate), β-TCP, octacalcium phosphate, amorphous calcium phosphate, and the like. Note that, when the implant is an artificial dental root, the root portion thereof can be exclusively sputter coated by sputtering the root part with the other portion being covered so as not to be sputter coated.

In the present invention, since the surface of the implant is roughened as explained above, it can be effectively coated with a calcium phosphate based material coating such as hydroxyapatite by sputtering. Furthermore, in this coating process, for example, highly refined hydroxyapatite is homogeneously coated on the surface, so the hydroxyapatite coating is not removed, thereby being able to obtain a preferred implant. This hydrothermal treatment is particularly effective when surface roughening is performed by using shot material containing fluoroapatite, and then a hydroxyapatite thin film is formed by sputtering. In the above described method for producing an implant, impurities are generated by sputtering. But by performing the above described hydrothermal treatment, the impurities can be removed. Also, hydroxyapatite coating which is formed by sputtering can be crystallized properly, thereby obtaining a preferred implant.

Japanese Patent Application Laid-Open Publication No. H04-168297 discloses a method for converting calcium phosphate into hydroxyapatite. The converting process is as follows. The surface of a base material is roughened by alumina and the like. Then the surface is coated with calcium phosphate by the plasma spraying method. And the hydrothermal treatment is performed on the resulting material in aqueous solution containing calcium and phosphoric acid. In this process, fine particle of calcium phosphate compound is generated in the hydrothermal solution. And this fine particle physically collides with a thin film of hydroxyapatite due to enhanced convective flow in the solution, which caused a problem of removing hydroxyapatite coating. As for a plasma-spray-generated hydroxyapatite coating, about 1 μm of exfoliation will not be a problem because it has more than 30 μm of film thickness. But as for sputter coated hydroxyapatite coating, about 1 μm of exfoliation will be a big problem because it has 1 to 2 μm of film thickness at most. Therefore hydrothermal treatment in an aqueous solution including phosphoric acid and calcium ions is not suitable for crystallization by removing impurities from hydroxyapatite layer obtained by sputter coating. There is another problem. About 10 mg of hydroxyapatite is dissolved in 1 L of purified water. Since the mass of 1 to 2 μm of sputter coated hydroxyapatite thin film is no more than 1 mg, all the hydroxyapatite thin film is dissolved in purified water. Due to this problem of hydroxyapatite solubility, purified water can not be used for hydroxyapatite thin film. In the present invention, since hydrothermal treatment is performed in alkali aqueous solution, hydroxyapatite thin film can be prevented from being dissolved, and also the crystallinity is increased. This is demonstrated in the examples described below.

For example, alkali aqueous solution from pH 9 to pH 11 is used for the hydrothermal treatment. As demonstrated in the example below, it may be from pH 9 to pH 11, it may also range from pH 9.5 to pH 10.5. These alkali solutions can be adjusted by adding alkali such as NaOH, KOH, NH$_4$OH, as appropriate. In the step of hydrothermal treatment, for example, an implant is soaked in alkali solution at the temperature range from 100° C. to 150° C. for from 3 hours to 24 hours. Since reaction speed of hydrothermal treatment is not improved over 120° C., the temperature range may be from 100° C. to 120° C., it may also be form 110° C. to 120° C. The hydrothermal treatment is also preferred to be performed under pressure. The example of the range of the pressure is from 1.1 to 20 atmospheric pressure. It may also be from 2 to 10 atmospheric pressure.

The implant produced by the method for producing implant of the present invention has roughened surface to which bones and the like are easily to be combined. It can also have a homogeneous and highly purified hydroxyapatite coating. In addition, the shot material which is left on the surface of an implant by the surface roughening by the sand blast method is also removed effectively. So the implant is superior in biocompatibility. Therefore, the implant produced by the method for producing an implant of the present invention can be used as an artificial bone or an artificial dental root effectively, by being embedded in vivo by surgical or dental operation.

Example 1

A screw shaped titanium 2 type of dyamiter 4 mm was assumed to be a dental root. In order to roughen the surface thereof, sandblast was performed. The shot material used in the sandblast treatment was prepared as follows. Each of synthesized fluoroapatite ceramics, synthesized hydroxyapatite ceramics, and natural mineral fluoroapatite (produced in Brazil) was grained in alumina mortars, and was granulated through sieves into four kinds: 14 to 22 (A), 22 to 30 (B), 30 to 84 (C) mesh and 84 under (D). For comparison, silica and alumina was also grained and granulated to the size of 14 to 22 mesh. Each of the five kinds of shot material was separately put in a sandblast apparatus, and the sandblast was performed on the surface of each three screw-shaped titanium under the pressure of 0.5 Pa.

Having performed the sandblast treatment, they were soaked in 6 N hydrochloric acid aqueous solution for 1, 3 or 5 minutes. Then they were examined by an energy dispersive X-ray fluorescence apparatus (EDX) to examine the remaining shot materials. As a result, it was confirmed that all the apatite shot materials were removed in a minute. On the other hand, silica and alumina were not dissolved in the acid, and 10 to 20% thereof remained on the surface of titanium, not being removed by water or alcohol washing. The arithmetic mean deviation of the profile (Ra) of the surface of titanium which was made by the apatite-based shot material having different particle sizes was measured by a surface roughness meter (Surfcom made by Tokyo Seimitsu Co.) under the conditions of an evaluation length of 0.8 mm, a measuring speed of 0.3 mm/sec, and a cutoff value of 0.8 mm. Each test was performed on the three implants. The mean values of the obtained surface roughness are shown in table 2.

TABLE 2

| Surface Roughness (Ra) Made by Each Shot Material (unit μm) | | | | |
|---|---|---|---|---|
| shot material | (A) | (B) | (C) | (D) |
| synthesized fluoroapatite | 3.5 | 2.0 | 1.5 | 0.5 |
| natural fluoroapatite | 5.0 | 3.0 | 2.5 | 1.8 |
| synthesized hydroxyapatite | 1.0 | 0.8 | 0.8 | 0.8 |

It can be seen from the table 2 that the surface roughness of titanium was maximized when natural fluoroapatite was used as a shot material, and the surface roughness was decreased in order of synthesized fluoroapatite, and synthesized hydroxyapatite. Natural fluoroapatite contains small amount of silica and alumina which are harder than apatite. Therefore, it was assumed that the titanium surface becomes a little bit rougher when natural fluoroapatite was used as shot material compared to when synthesized fluoroapatite was used as shot material. It can be seen that when synthesized hydroxyapatite was used as shot material, titanium surface roughness was not influenced by the particle size of synthesized hydroxyapatite. As a result, in order to adjust surface roughness in the range from 1 μm to 3 μm wherein osteogenesis is promoted, synthesized fluoroapatite is suitably be used, and then natural fluoroapatite is preferred to be used.

Example 2

With the sputtering method, hydroxyapatite was coated on the surface of 21 pieces of screw shaped titanium, whose surface was roughened by the synthesized fluoroapatite shot material in the example 1. The coating was performed so that the thickness became in the range from 1 to 2 μm. And then, the thickness of the hydroxyapatite coating was measured by energy dispersive X-ray fluorescence apparatus (EDX). Also, the crystalline phase of the hydroxyapatite coating was measured by X-ray diffractometer (XRD).

1000 mL of alkali aqueous solution was prepared which was adjusted with caustic soda of pH 7, 8, 9, 9.5, 10, 10.5, and 11. Each of three dental roots, which was coated with hydroxyapatite by the sputtering method was put in the alkali aqueous solution, and was hydrothermally treated at 110° C. for 20 hours. After the hydrothermal treatment, the thickness of the hydroxyapatite coating was measured by EDX. Also, the crystalline phase of the hydroxyapatite coating was measured by X-ray diffractometer (XRD). As a result, it was confirmed that a coating layer, which was not thermally treated, contained hydroxyapatite and impurities, but after the thermal treatment, the impurities had been removed from the coating layer. The impurities contained tricalcium phosphate (TCP) calcium pyrophosphate, calcium oxide, and the like. And the total amount of impurities was 10 to 20 percent by weight. According to the results of XDR measurement performed on the crystalline phase exclusively composed of hydroxyapatite, in the condition of equal to or more than pH 9, X-ray diffraction pattern was sharpened and crystallinity of hydroxyapatite was improved. When aqueous solution of neutral pH (pH 7 to 8) is used, the thickness of the coating was decreased by 30 to 50 percent, and when the pH was 9, the thickness thereof was decreased by about 5 percent. When the pH was over 9.5, the decrement was not observed. Therefore, it was conceived that the alkali hydrothermal treatment was suitably performed at equal to or more than pH 9, and was optimally performed at equal to or more than pH 9.5.

Example 3

An alkali hydrothermal treatment under atmospheric pressure at 90 to 100° C., and a pressurized alkali hydrothermal treatment using an autoclave at 100 to 150° C. were performed. In the former case, the reaction speed of removing impurities from hydroxyapatite coating was low, and the crystallinity of hydroxyapatite was also low. In the latter case, however, the reaction speed was doubled compared to that of the former case, and the crystallinity was also improved. On the other hand, there was no remarkable improvement observed when the pressurized alkali hydrothermal treatment was performed at over 120° C.

Example 4

A surface roughening was performed on the surface of plate-like titanium 2 type of 1 cm×2 cm×0.5 cm assuming a bone plate. It was performed so that the Ra became 1 μm by using fine shot material of synthesized fluoroapatite whose grain size is from 30 to 84 mesh. Hydroxyapatite of 1.5 μm was coated on the surface thereof by the sputtering method. And three pieces of the resulting plate-like titanium were put in alkali aqueous solutions of 1000 mL which were adjusted to pH 9 and 9.5 and containing phosphoric acid and calcium ion of about 0.001% and 0.01%. The hydrothermal treatment was performed at 110° C. for 20 hours, and then the thickness of hydroxyapatite coating was measured with EDX. As the result, the thickness of the hydroxyapatite coating was reduced by the range of 20 to 50%. The higher the concentration of phosphoric acid and calcium ion, and the higher the level of the pH, the larger amount of suspending calcium phosphate particles were generated. It was considered that the particles collided with the hydroxyapatite coating in strong convection currents in the hot water, exfoliating a large portion of the hydroxyapatite coating.

The present invention can be used as a method for producing an implant such as an artificial dental root.

What is claimed is:

1. A method for producing an implant comprising a step of roughening a surface of an implant by a sand blast method,
    wherein the step of roughening includes a step of colliding a shot material with the surface of the implant, the shot material comprising fluoroapatite, further comprising:
        a step of removing the shot material, performed after the step of roughening, by putting acid on the implant, the shot material being collided with the surface of the implant and attached thereto,
wherein the acid is a hydrochloric acid aqueous solution with a concentration ranging from 1 N to 6 N, or a nitric acid aqueous solution with a concentration ranging from 1 N to 6 N,
        a coating step of sputter coating a calcium phosphate based material film on the implant, the thickness of the film being from 1 to 2 micrometers, after the step of removing the shot material, and
        a hydrothermal treatment step using an alkali aqueous solution, performed after the coating step,
            wherein the alkali aqueous solution consists of one or more alkaline compounds selected from the group consisting of NaOH, KOH and NH4OH and a pH range of the alkali aqueous solution is equal to or more than pH 9, and
            wherein the implant is soaked in the alkali aqueous solution at a temperature ranging from 100° C. to 150° C. for 3 hours to 24 hours under 2 to 10 atmospheric pressure.

2. The method for producing an implant as claimed in claim 1, wherein the step of roughening is a step to roughen the surface of the implant so that an arithmetic mean deviation of Ra of the surface of the implant becomes in a range from 0.3 μm to 3 μm.

3. The method for producing an implant as claimed in claim 1, wherein the shot material comprising fluoroapatite is screened with a screen having mesh openings from 12 to 100 mesh.

4. The method for producing an implant as claimed in claim 1, wherein the implant is an artificial dental root.

5. The method for producing an implant as claimed in claim 1,
    wherein the implant is an artificial dental root, and
    wherein the step of roughening is a step to roughen a surface of the root part of the artificial dental root so that an arithmetic mean deviation of Ra of the surface of the root part of the artificial dental root becomes in a range from 0.3 μm to 3 μm.

6. The method for producing an implant as claimed in claim 1,
    wherein the acid is a hydrochloric acid aqueous solution with a concentration ranging from 1 N to 6 N, or a nitric acid aqueous solution with a concentration ranging from 1 N to 6 N, and
    wherein the step of removing the shot material comprises a step of soaking the implant into the hydrochloric acid aqueous solution or the nitric acid aqueous solution for 1 minute to 10 minutes.

7. The method for producing an implant as claimed in claim 1,
    wherein the pH range of the alkali aqueous solution is from pH 9 to pH 11.

8. The method for producing an implant as claimed in claim 1,
    wherein the implant comprises Ti.

9. The method of claim 1, wherein the hydrothermal treatment step removes impurities.

10. A method for producing an artificial dental root comprising:
    a step of roughening a surface of the artificial dental root by a sand blast method,
        wherein the step of roughening includes a step of colliding a shot material with the surface of the artificial dental root, the shot material comprising fluoroapatite,
        wherein the surface of a root part of the artificial dental root is roughened so that an arithmetic mean deviation of Ra of the surface of the root part of the artificial dental root becomes in a range from 0.3 μm to 3 μm, and
        wherein the shot material comprising fluoroapatite is screened with a screen having mesh openings from 12 to 100 mesh,
    a step of removing the shot material, performed after the step of roughening the surface of the artificial dental root, by putting an acid on the artificial dental root, the shot material being collided with the surface of the artificial dental root and attached thereto,
        wherein the acid is a hydrochloric acid aqueous solution with a concentration ranging from 1 N to 6 N, or a nitric acid aqueous solution with a concentration ranging from 1 N to 6 N, and
        wherein the step of removing the shot material comprises a step of soaking the artificial dental root into the hydrochloric acid aqueous solution or the nitric acid aqueous solution for 1 minute to 10 minutes,
    a coating step for sputter coating a hydroxyapatite film on the artificial dental root after the step of removing the shot material, and
    a hydrothermal treatment step performed with an alkali aqueous solution, performed after the coating step,
        wherein the alkali aqueous solution consists of one or more alkaline compounds selected from the group consisting of NaOH, KOH and NH4OH and a pH range of the alkali aqueous solution is from pH 9 to pH 11, and wherein the artificial dental root is soaked in the alkali aqueous solution at a temperature ranging from 100° C. to 150° C. for 3 hours to 24 hours under 2 to 10 atmospheric pressure.

11. The method for producing an implant as claimed in claim 10, wherein the implant comprises Ti.

* * * * *